(12) United States Patent
Flohr et al.

(10) Patent No.: US 6,381,487 B1
(45) Date of Patent: Apr. 30, 2002

(54) METHOD AND APPARATUS FOR PRODUCING CT IMAGES

(75) Inventors: Thomas Flohr, Uehlfeld; Bernd Ohnesorge, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/451,228

(22) Filed: Nov. 29, 1999

(30) Foreign Application Priority Data

Nov. 27, 1998 (DE) .......................................... 198 54 939

(51) Int. Cl.⁷ ................................................. A61B 5/05
(52) U.S. Cl. ....................... 600/425; 600/509; 600/522; 378/4; 378/21; 378/23; 378/27
(58) Field of Search ................................ 600/425, 426, 600/407, 408, 509, 522; 324/309; 378/4, 8, 21, 98, 29, 27; 250/401, 402, 403, 445, 320, 362, 363.01–363.05

(56) References Cited

U.S. PATENT DOCUMENTS 4,149,249 A * 4/1979 Pavkovick
4,182,311 A 1/1980 Seppi et al.
4,641,328 A 2/1987 Fujise
4,994,965 A * 2/1991 Crawford et al.
5,751,782 A 5/1998 Yoshitome
6,154,516 A * 9/1998 Heuscher et al.
5,832,051 A 11/1998 Lutz
5,991,356 A * 11/1999 Horiuchi et al.

FOREIGN PATENT DOCUMENTS

EP            0 370 341            5/1990

* cited by examiner

Primary Examiner—Marvin M. Lateef
Assistant Examiner—Jeoyuh Lin
(74) Attorney, Agent, or Firm—Schiff Hardin & Waite

(57) ABSTRACT

In a method and CT apparatus for producing CT images of a body region periodically moving with resting or motion phases, data corresponding to a number of projections serving the purpose of imaging are analyzed to determine whether each projection was acquired during a resting or motion phase, and only those data that were acquired during a resting phase are employed for image reconstruction.

32 Claims, 14 Drawing Sheets

IMAGE 1: START PROJECTION 50
IMAGE 2: START PROJECTION 150
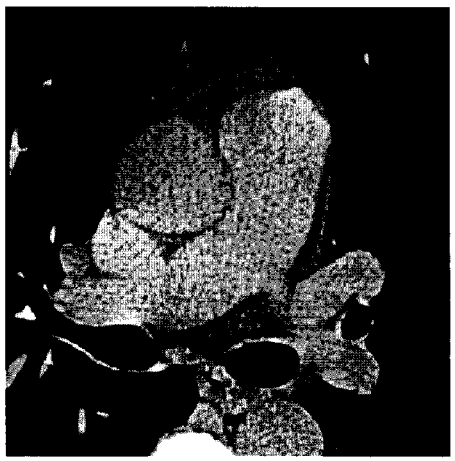
IMAGE 3: START PROJECTION 250
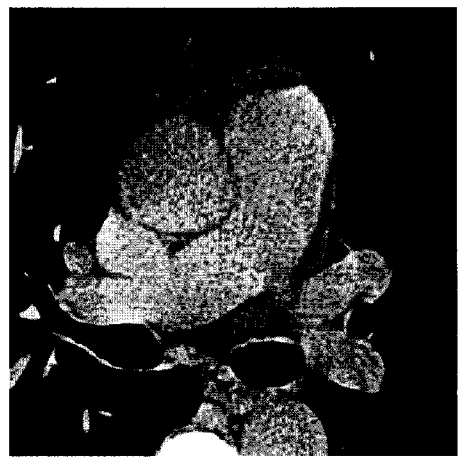
IMAGE 4: START PROJECTION 350
FIG 7

METHOD AND APPARATUS FOR PRODUCING CT IMAGES

BACKGROUND OF THE INVENTION

1. Field of the Invention

The present invention is directed to a method for producing computed tomography (CT) images of a body region periodically moving with resting and motion phases with a CT apparatus having an x-ray source moved around the body of the life form to be examined for producing the CT images, and is also directed to an apparatus for the implementation of such a method.

2. Description of the Prior Art

Subjects that move during the CT data registration often cause line artifacts in the reconstructed CT image or are presented unsharp with double contours. This problem particularly occurs given CT exposures of the heart or heart-proximate lung structures in CT systems having mechanical movement of the x-ray source, wherein the data registration time for an image lies on the order of magnitude of one heart cycle. The motion artifacts are then caused by the employment of data for image reconstruction that were registered during the rapid contraction phase of the heart. Such images can only be conditionally employed for medical diagnostic interpretive methods such as, for example, calcification screening or perfusion imaging.

CT images of the heart that are relatively low in motion artifacts can be acquired with electron beam computer tomography (EBT). The x-ray source can be move free of inertia by electromagnetic deflection of an electron beam. Significantly shorter data registration times and, thus, a reduction of the motion artifacts, thus can be achieved. The cost of an EBT system, however, are multiply higher than that of a convention CT apparatus. Moreover, the image quality obtainable with an EBT—apart from cardiac images low in motion artifacts—cannot compete with that of a conventional system.

Conventional CT systems of the third and fourth generations have a mechanical rotation of the x-ray source and currently achieve scan times below 1 second per 360° revolution (full revolution). An adequately good image quality for heart exposures can be achieved with such systems when only the data measured during the resting phase of the heart are employed for the image reconstruction.

One possibility for achieving this demand is offered, for example, by the ECG-triggered CT exposure technique disclosed in European Application 0 370 341 and German OS 196 27 166. The R-waves of an ECG signal obtained while image data are being registered serve for triggering the data registration. The measurement of a sub-revolution or full revolution starts after recognition of a registered R-wave, namely with an empirically defined delay time relative to the R-wave. A shutoff of the radiation likewise triggered by the ECG does not ensue at the end of the resting phase of the heart.

Other methods disclosed, for example, in German PS 33 25 939 and U.S. Pat. No. 4,182,311 forgenerating heart images register the ECG signal during the measurement and employ only data from a specific heart phase for the image reconstruction insofar as possible. The determination of the desired region thereby ensues purely empirically according to standard values known from the literature. This is also true of what has become the standard ECG-triggered CT exposure technique, wherein the delay time is likewise only empirically determined. Such a method is disclosed in German PS 196 22 075. A disadvantage of the method with empirical definition of the delay time, or of the part of the heart cycle with respect whereto data are used, is the highly different correlation of the ECG signal and mechanical heart movement for various patients.

SUMMARY OF THE INVENTION

An object of the present invention is to provide a method and an apparatus of the type initially described wherein the risk of the occurrence of motion artifacts is diminished.

The above object is achieved in accordance with the principles of the present invention in a method and an apparatus for producing CT images of a body region which periodically moves with resting and motion phases, wherein an x-ray source focus is moved around the body of the subject under examination for registering data used for producing the CT images, and wherein a number of projections are registered, during at least one revolution of the x-ray source focus around the subject, preferably, and during a time duration that is at least equal to a cycle of the movement of the body region, and wherein the projection data are analyzed directly to determine whether the data were acquired during a resting phase or a motion phase, and wherein only those data are employed for image reconstruction that were found to be acquired during a resting phase.

The inventive method is thus an automatic method wherein the registered measured data are patient-specifically classified by analysis of the measured data themselves to determine whether they are usable, i.e. were acquired during a resting phase of the heart, or are unusable, i.e. were acquired during a motion phase, with only measured data acquired during a resting phase of the heart being utilized for the image reconstruction. The inventive method can be applied for arbitrary CT apparatuses of the third or fourth generations having one or more detector lines, namely for normal axial scans as well as for spiral scans. The projections classified as usable according to the inventive method can be employed for arbitrarily fashioned reconstruction methods.

In one version of the invention, for classification of the measured data, the ECG signal of the respective patient is utilized. The correlation of the ECG signal with the actual mechanical movement of the heart can, first, ensue with automatic or interactive evaluation of measured data and/or CT images of a reference examination, i.e. a number of test projections, and evaluation of the synchronously acquired ECG signal. In this way, the patient-specific delay between R-wave of the ECG signal and the trigger time of the radiator can also be quantitatively acquired for ECG-triggered CT exposures, leading to a significantly improved imaging and a significantly more efficient examination execution.

Thus, with the inventive apparatus, an operator has the possibility of interactively identifying specific images as being low in motion artifacts.

DESCRIPTION OF THE DRAWINGS

FIG. 7 shows graphic examples of the automatic determination of the resting heart phase.

DESCRIPTION OF THE PREFERRED EMBODIMENTS

As is well-known from the applicable literature, there is a correlation between the ECG signal and actual mechanical heart muscle contraction and heart muscle relaxation of a subject. Measured data, for example, projections, that are acquired during the relatively short phases with especially pronounced movement are not suitable for a low-artifact image reconstruction and must be classified as unusable for the reconstruction. Only those images for which measured data that are acquired or were acquired during phases of little movement classified as employable are available for image reconstruction. Dependent on the possibilities of the CT apparatus employed, axial reconstruction from measured data acquired in a full revolution or subrevolution as well as spiral reconstruction (given adequate data coverage) can occur, for one or more detector lines.

Figure 1:
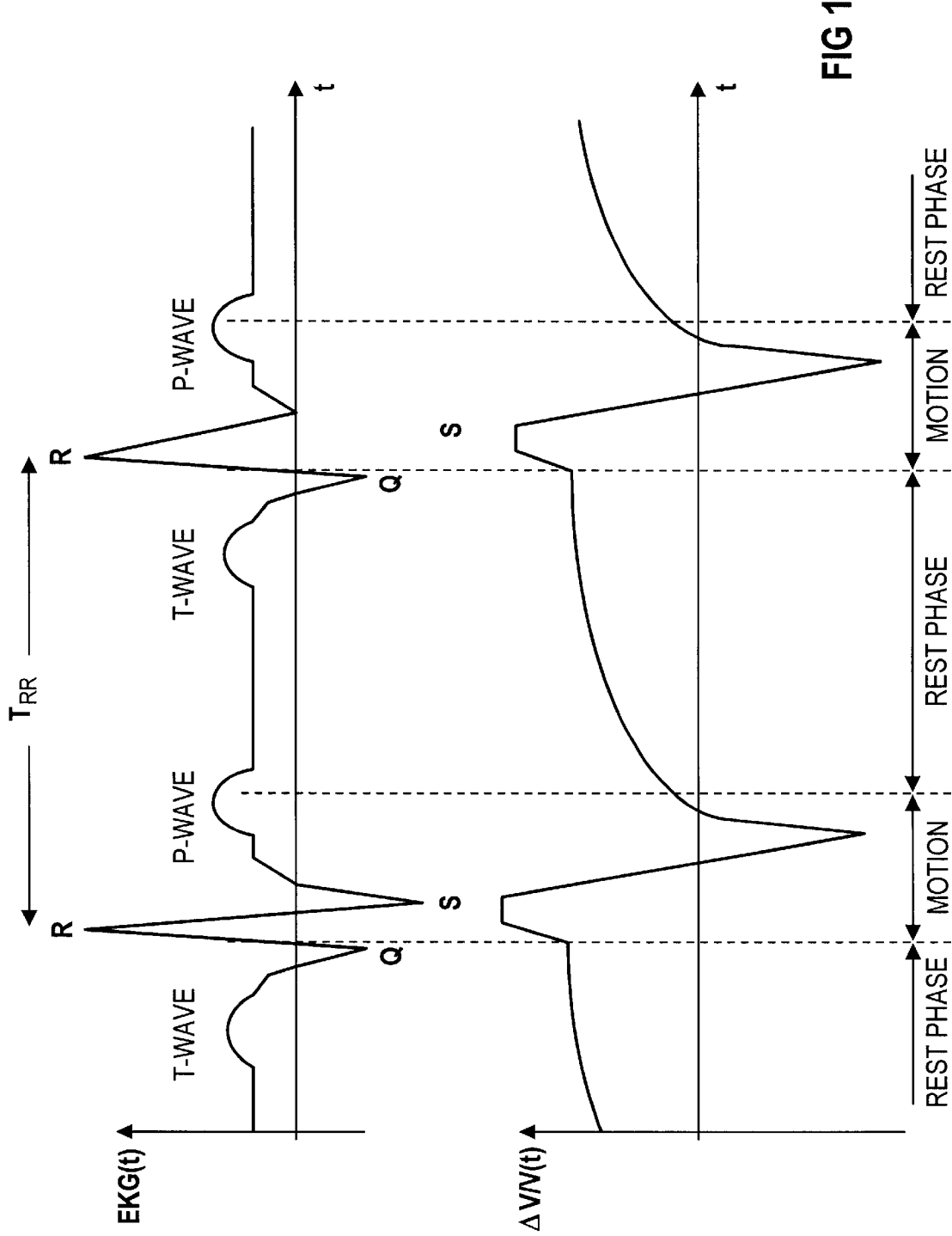
FIG. 1 shows the correlation of an ECG signal and mechanical heart movement, with the ECG signal and the mechanical heart movement, quantified by the relative volume change $\Delta V/V$ of the heart chambers, being shown as function of the time.

FIG. 1 shows the fundamental correlation of ECG signal and mechanical heart movement during a cycle with the RR interval $T_{RR}$. The mechanical heart movement is quantified by the relative volume change $\Delta V/V$ of the heart chambers.

It is particularly the time reference between the P-wave and the QRS complex in the ECG signal that differs from patient to patient together with the mechanical contraction of the heart chambers that influences the termination of the reconstruction time intervals usable for image calculation, i.e. those time intervals from which the measured data employed for reconstruction of an image originate.

The relative position of the mechanical resting phase of the heart in relation to the ECG signal can be determined with a reference examination (scan).

Images that are to be allocated to immediately successive points in time are reconstructed from the measured data with respect to a suitable heart slice that cover at least one heart cycle, preferably a few heart cycles, given at least one revolution, preferably a very few revolutions, of the x-ray source around the examination subject. The point in time of an image is the time mid-point of the data employed for the reconstruction. It is then assumed that only data from the resting phase of the heart have contributed to images of the reference examination that are low in motion artifacts. By contrast, images that are based on projections registered during the motion phase exhibit highly visible motion artifacts.

Figure 2:
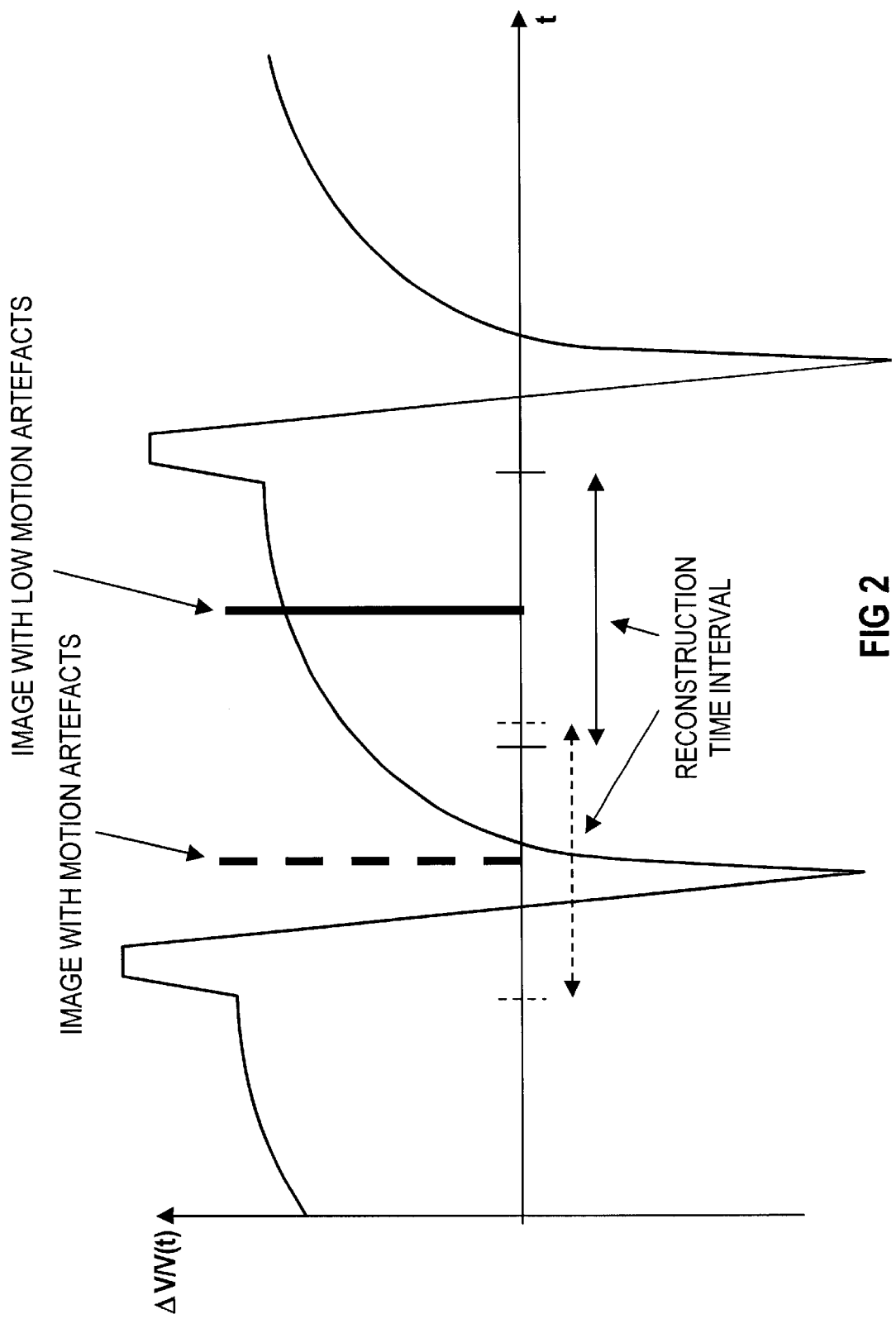
FIG. 2 shows projection intervals of images low in motion artifacts.

FIG. 2 shows the time allocation of the reconstruction time intervals belonging to the various reconstructed images relative to the time curve of the relative volume change $\Delta V/V$. The time interval corresponding to the resting phase of the heart during a heart cycle can be identified on the basis of a division of reconstructed images into image sequences having few and having more pronounced motion artifacts, or on the basis of an analysis of the measured data. For example, the position of the resting phase of the heart relative to the ECG signal can be estimated from a reference examination by identifying a time interval, during which projections were acquired in the resting phase of the heart, within the reference examination by selecting an image sequence low in motion artifacts.

The reference examination, moreover, can ensue at a reduced radiation dose.

An automated allocation of the measured data to the resting phase and to the motion phase of the heart, which is yet to be explained, also offers the possibility of designational, retrospective reconstruction of images in the resting phase of the heart without an ECG signal registered in parallel.

Figure 3:
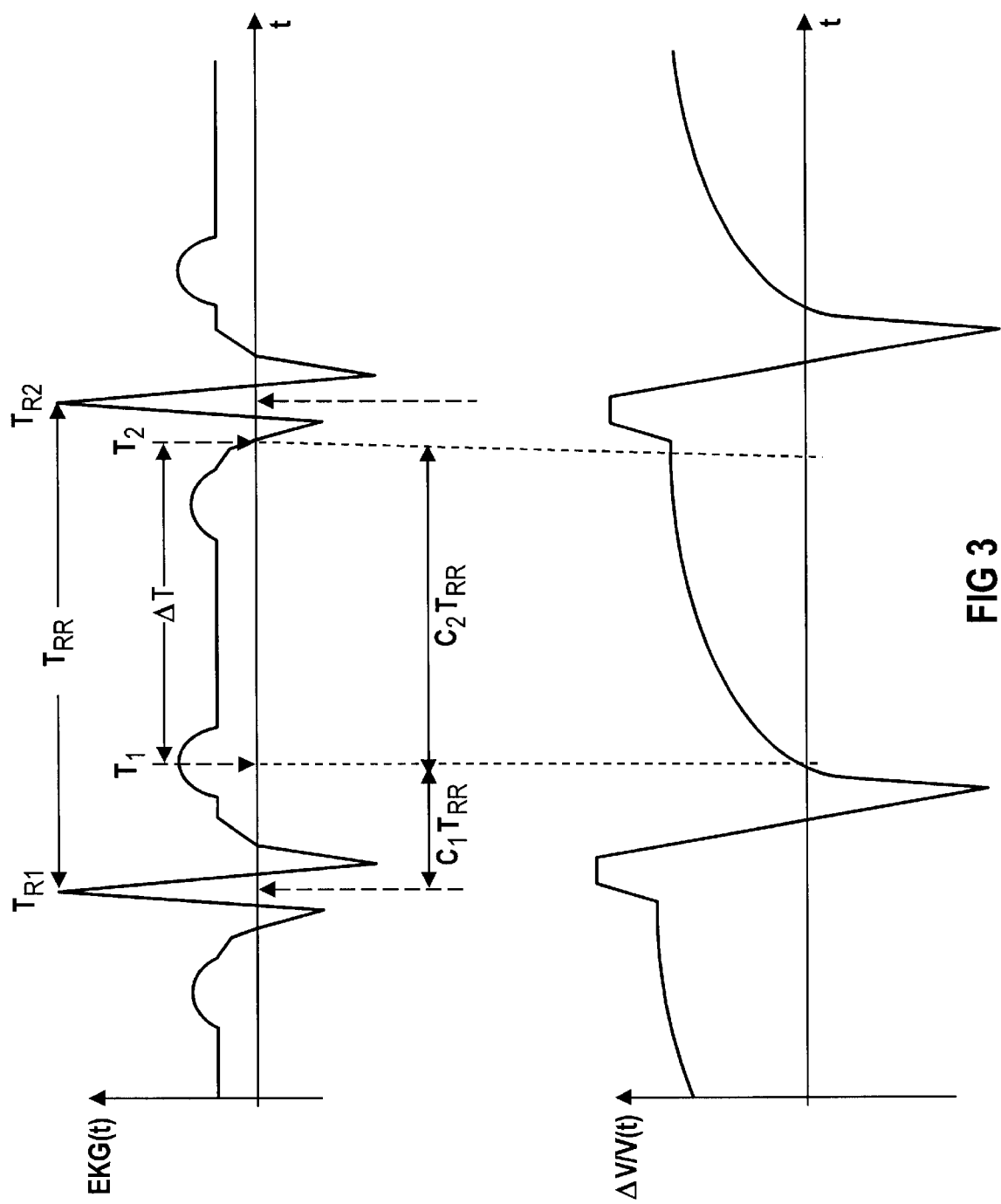
FIG. 3 shows the parametrization of the resting heart phase dependent on the R-wave-to-R-wave (RR) interval.

According to FIG. 3, the resting phase of the heart lies in an interconnected time interval $[T_1,T_2]$ having the length $\Delta T=T_2-T_1$ between two successive R-waves of the ECG signal. The relative position of the resting phase of the heart in the respective RR interval $T_{RR}$, i.e. in the heart cycle limited by the R-waves registered at times $T_{R1}$ and $T_{R2}$, can be described by two constants $C_1$ and $C_2$, namely:

$$T_1=T_{R1}+C_1T_{RR},\ T_2=T_1+C_2T_{RR}. \quad (1)$$

Figure 4:
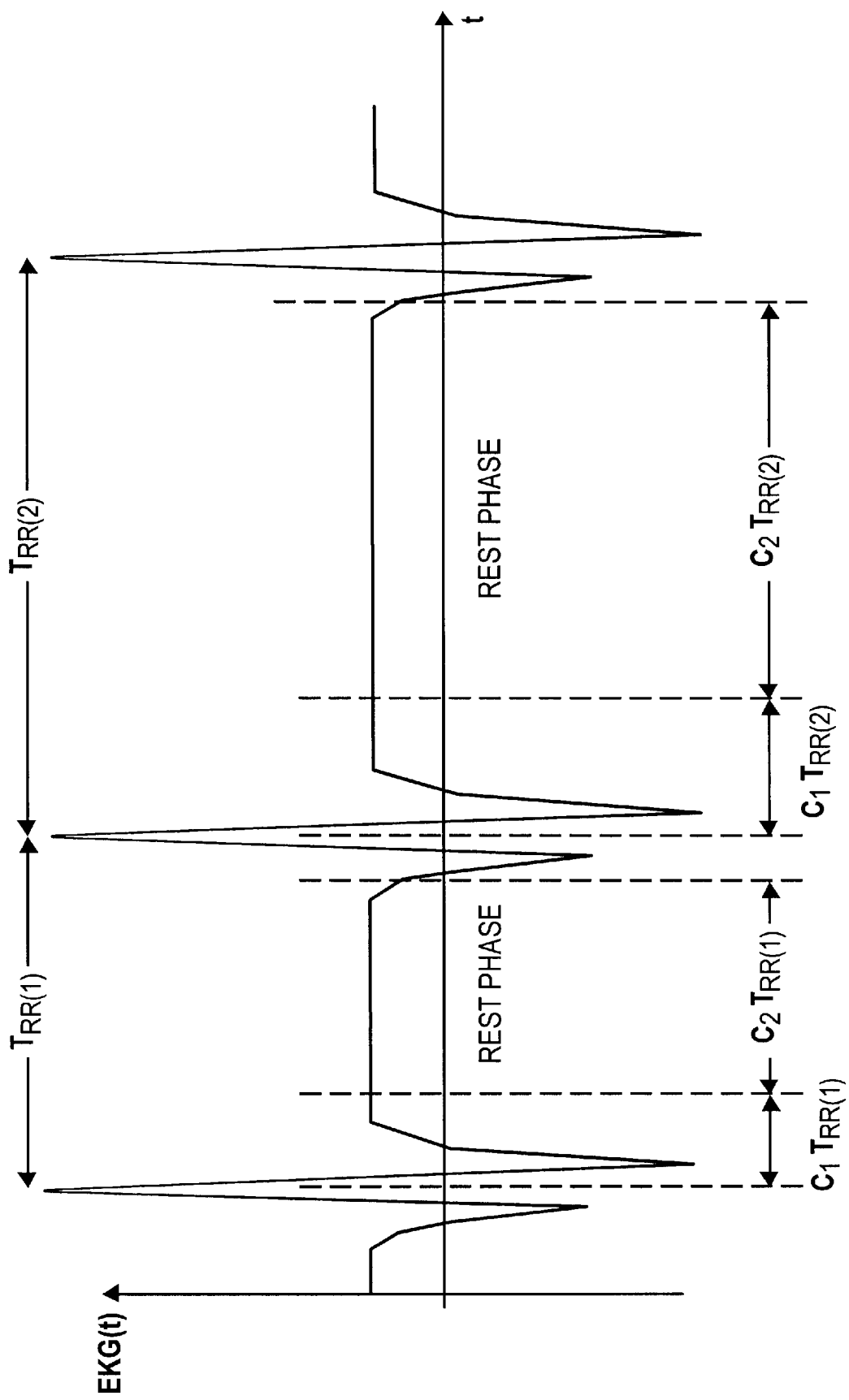
FIG. 4 illustrates the derivation of the resting phases of the heart from RR intervals.

The constants $C_1$ and $C_2$, which are fractions of the duration of the respective RR interval, are patient-specific and must be identified from the reference examination with suitable quantitative interpretation before the actual examination. The constants $C_1$ and $C_2$ are assumed not to change for the subsequent actual examination. The position in time and the duration of the resting phase of the heart then can be derived at any time from the duration of the currently existing RR interval $T_{RR}$. FIG. 4 illustrates this procedure with reference to the example of RR intervals of variable duration.

Figure 5:
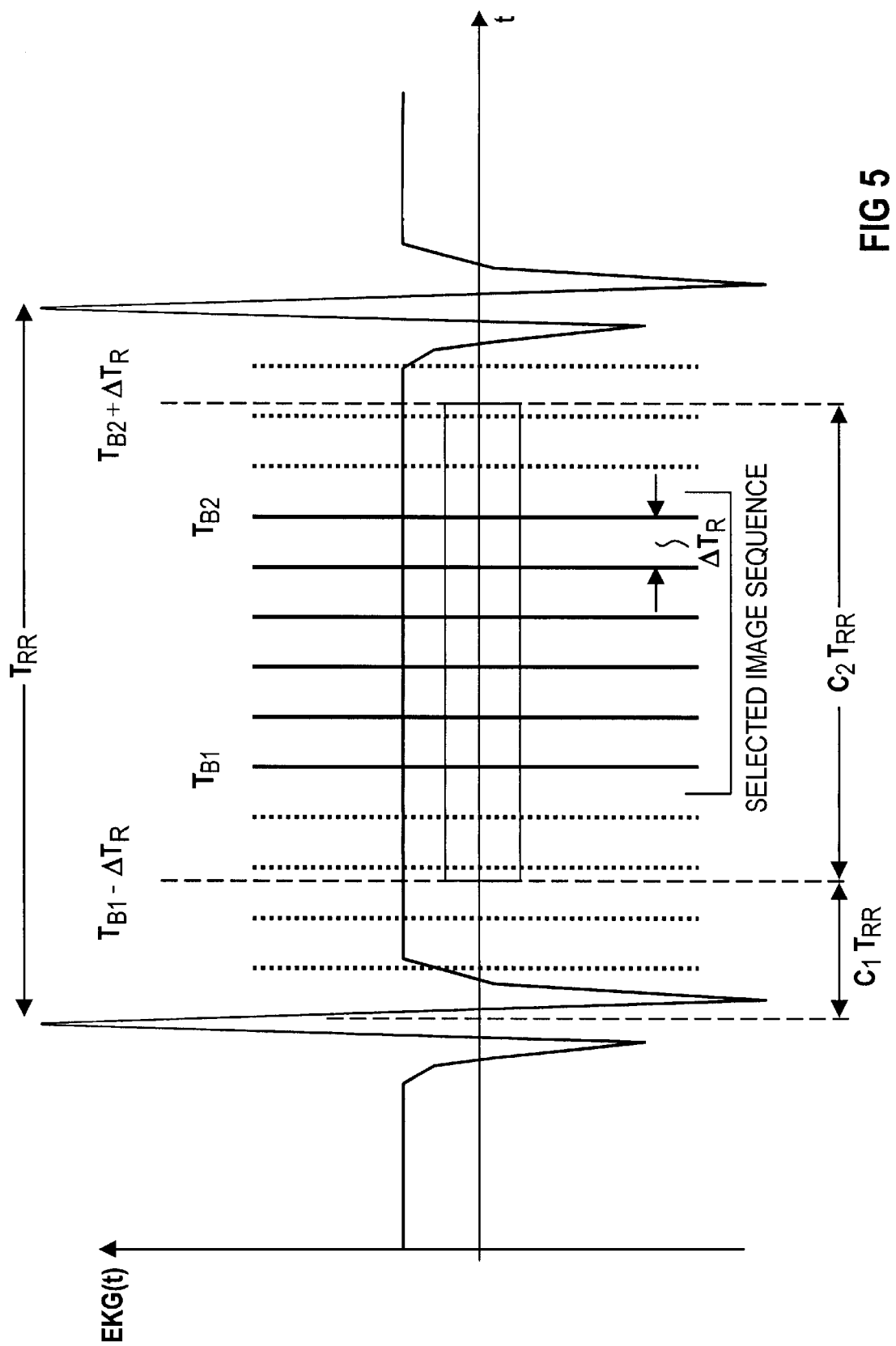
FIG. 5 illustrates the determination of the resting heart phase with interactive selection of an image sequence low in motion artifacts from the reference examination.

A further possibility for determining the resting phase of the heart relative to the ECG signal is the interactive selection by an operator of image sequences of the reference examination with few motion artifacts. Images from the data of the overall reference examination are thereby calculated, for example by sub-revolution reconstruction, at immediately successive times $T_B=i\Delta T_B$. Measured data from the respective reconstruction time interval $[T_B-\Delta T_R, T_B+\Delta T_R]$ contribute to an image at the time $T_B$. An image sequence with few motion artifacts in the time interval $[T_{B1}, T_{B2}]$ defines the resting phase of the heart for the current RR interval in the time interval $[T_{B1}-\Delta T_R, T_{B2}+\Delta T_{TR}]$. In this way, too, the constants $C_1$ and $C_2$ can then be determined, as shown in FIG. 5.

In addition to a method with interactive image selection, a determination of the resting phase of the heart with the parameter $C_1$ and $C_2$ can ensue by automatic analysis of the reconstructed reference images or of the measured data.

Such an automatic analysis can, for example, be implemented as a comparison of complementary projections in parallel geometry. Complementary parallel projections belong to projection angles offset by 180°. Since current CT apparatuses usually register fan projectors, the parallel projections must first be produced therefrom by suitable interpolation and sorting rules, for example known re-binning techniques. A parallel projection also combines measured values from fan projections measured at different times. For example, the measuring time of its central channel can be defined as the measuring point in time of a parallel projection. Given a symmetrical detector with a number of detector elements arranged in a line corresponding in number to the number of measuring channels, the symmetry theorem applies for complementary parallel projections P(n,k) in the case of a stationary subject, resulting in $$P(N+n, K-k-1) = P(n,k) \ (N=0(1)(N-1), \ k=0(1)(K-1)) \quad (2)$$

wherein n: projection number, k: channel number (continuous numbering of the detector elements, whereby the central channel is the middle channel), N: plurality of parallel projections measured per 180° revolution angle, and K: plurality of channels per parallel projection.

Given an immobile subject, the difference P(N+n,K-k-1)-P(n,k) is equal to 0. The deviation of the difference from 0 is thus a criterion for the movement of the measured subject in the time $T_{ROT}/2$ (half the revolution time of the radiation source) during a half-revolution between the projections n and n+N. A suitable dimensional number is, for example, the sum of absolute deviations of the complementary parallel projections $\sigma_c(n)$ with:

$$\sigma_c(n) = SUM_{(k=Ka(1)Ke)}\{ABS[P(N+n,K-k-1)-P(n,k)]\} \quad (3)$$

The start and end channels $K_a$ and $K_e$ determine an interior region of the measuring field in which it is anticipated the heart is registered When the error criterion $\sigma_c(n)$ for a parallel projection n lies below a specific threshold $\sigma_{C,S}$, then it can be assumed that the projections [n,n+N] were registered during the resting phase of the heart.

Figure 6:
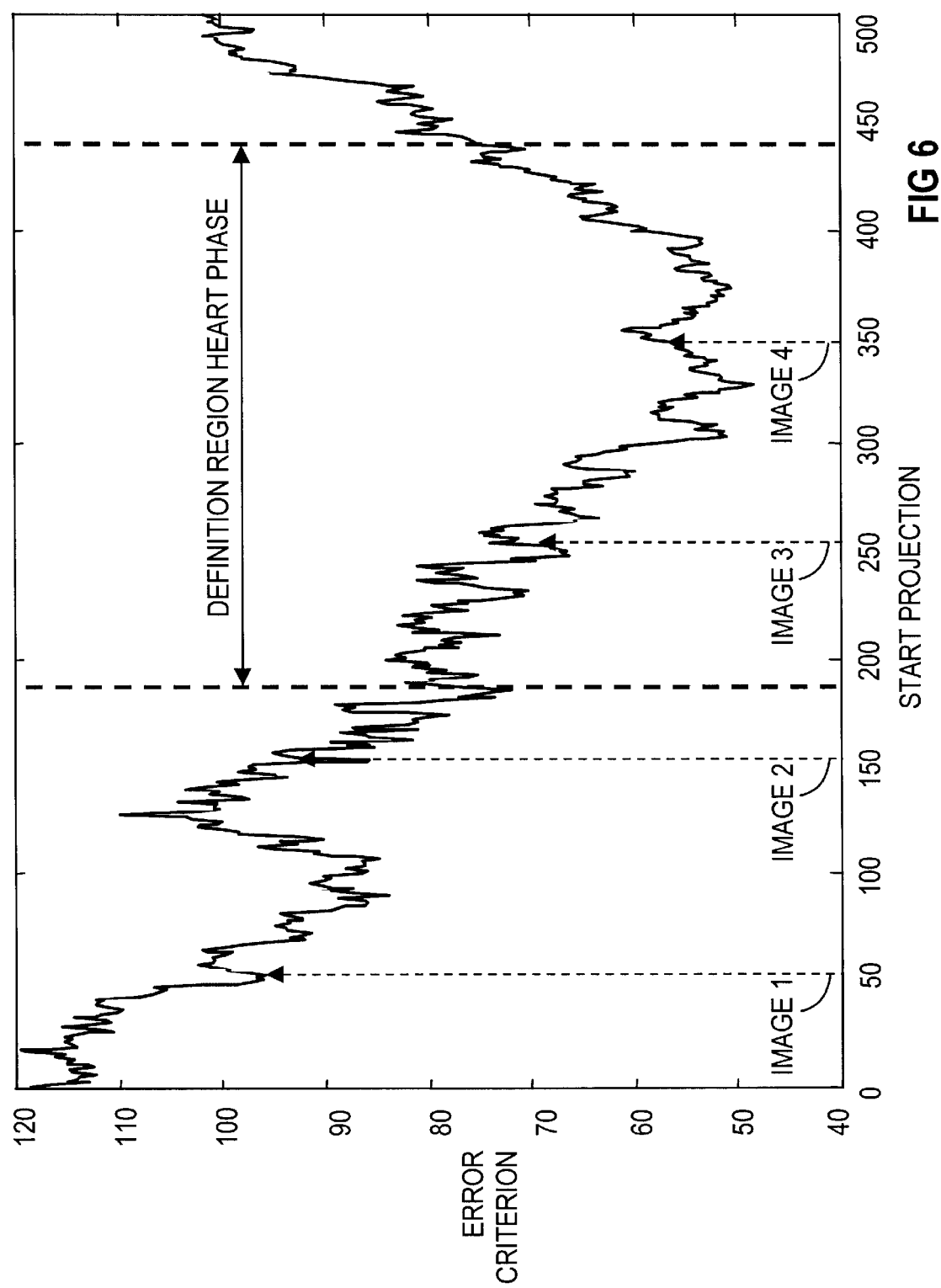
FIG. 6 shows the definition of the resting heart phase with a complementary data error criterion $\sigma_c$.

As an example, FIG. 6 shows the curve of the complementary error criterion $\sigma_c(n)$ for 500 parallel projections with N=528 as function of the start projection. By applying a threshold $\sigma_{C,S}$, an interconnected projection interval [$N_1$, $N_2$] (≈[185,440]) is identified that defines the resting phase of the heart in a time interval that corresponds to the time interval wherein the projections were registered in the interval n∈[$N_1$,$N_2$+N].

Images 1 through 4 are shown in FIG. 7, these having been reconstructed from the projections n ∈ [$N_{o,i}$, $N_{o,i}$+N−1] with the start projections $N_{o,i}$(i=1(1)4) marked in FIG. 6. The images demonstrate the significant correlation of the introduced error criterion $\sigma_c(n)$ with the extent of motion artifacts. Image 1 and image 2 show clear double contours of the heart chambers, whereas image 3 and image 4 exhibit hardly any motion artifacts.

Figure 8:
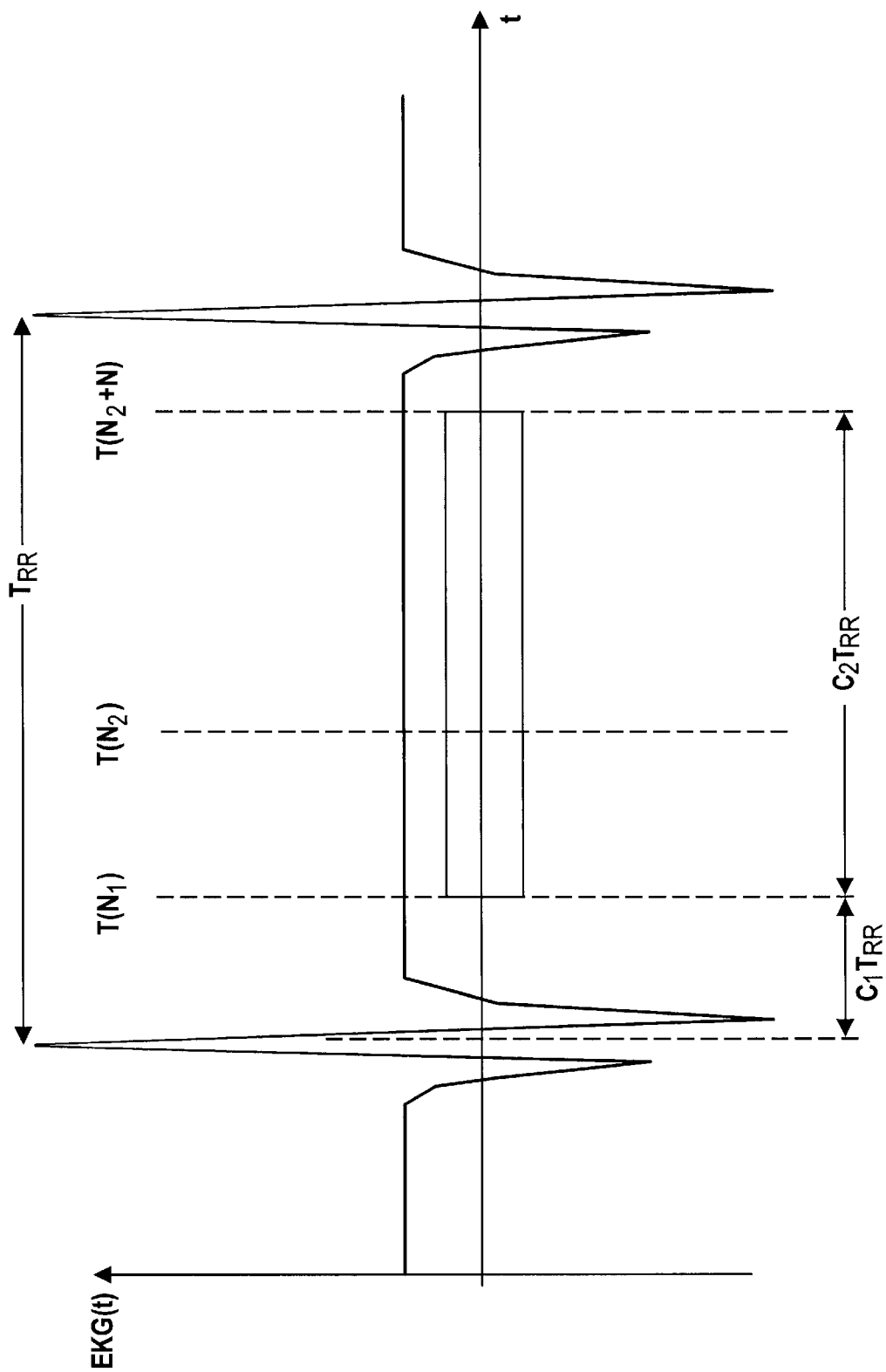
FIG. 8 shows the determination of the resting heart phase in the ECG signal with a data error criterion $\sigma_c$.

From the projection interval [$N_1$,$N_2$], the resting phase of the heart identified in FIG. 8 by hatching, can be defined from the projection interval n ∈ [$N_1$,$N_2$+N] in the time interval [$T_1 T_2$]=[T($N_1$),T($N_2$+N)]. The constants $C_1$ and $C_2$ according to (1) are again used for parametrization.

Apart from the automatic analysis of complementary data, an automatic interpretation of reconstructed images is also possible in the scope of the invention. When, for example, the differences of images succeeding one another in time exhibit a negligible extent of line artifacts or double contours, these images can be allocated to a resting phase of the heart. An uninterrupted sequence of images evaluated in this way as being low in motion artifacts then defines a resting phase of the heart.

Figure 9:
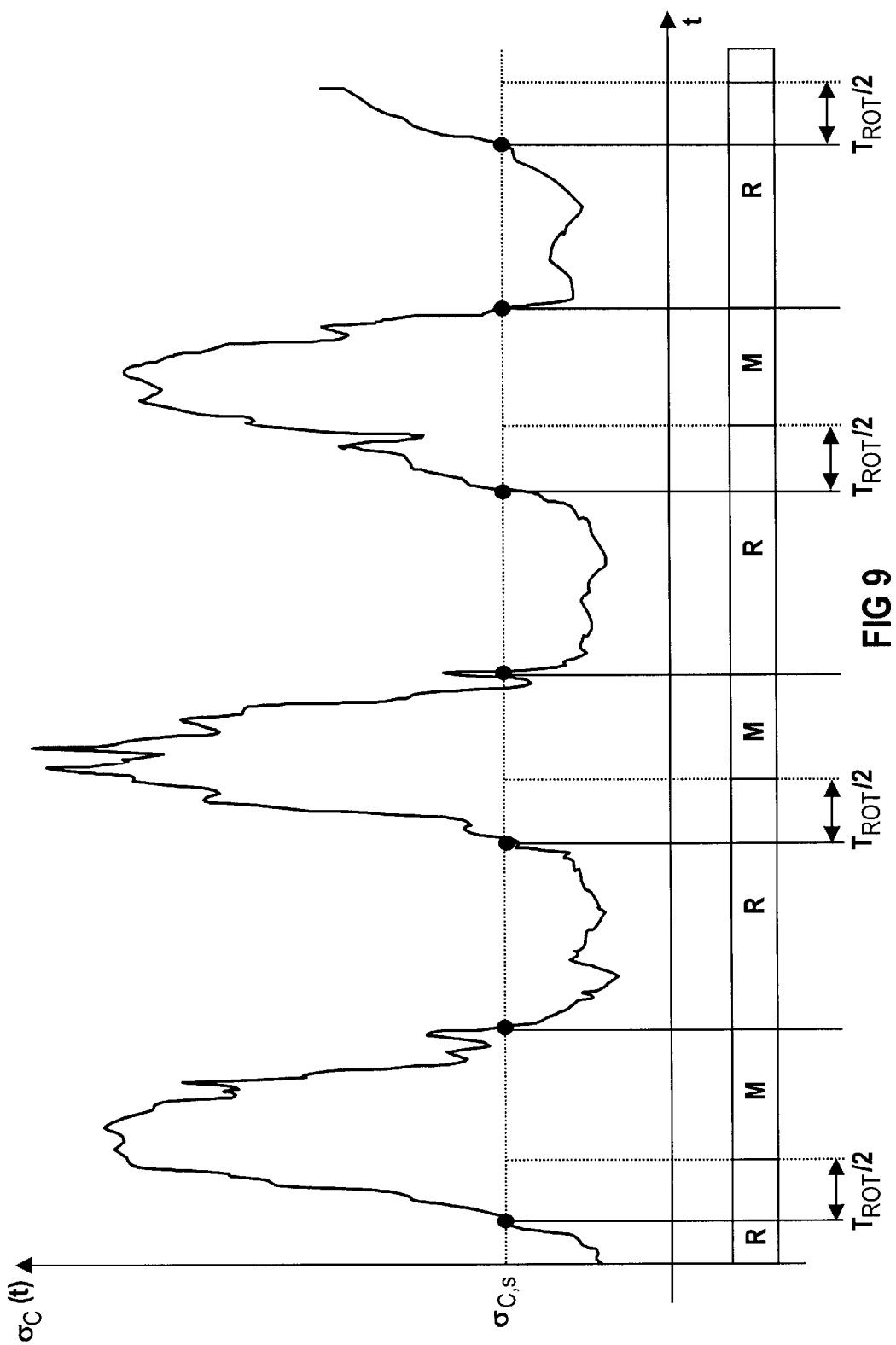
FIG. 9 shows the automatic determination of data intervals during the resting heart phase without ECG signal.

An ECG registration during the examination can also be entirely foregone when an automatic determination of projection intervals lying in the resting phase of the heart ensues, for example, with complementary data analysis. The reference examination is then limited to the registration of a suitable slice of the heart and to the selection of a suitable subject excerpt of this exposure, with respect to which the automatic determination of projection intervals lying in the resting phase of the heart ensues. The complementary error criterion $\sigma_C(t)$ for this is then calculated "on line" during the examination. For an exemplary curve of the complementary error criterion $\sigma_C(t)$, FIG. 9 shows how the regions of little movement are identified by application of a threshold $\sigma_{C,S}$, projection intervals lying in the resting phase of the heart being able to be derived therefrom and half the revolution time $T_{ROT}/2$ having also to be respectively added thereto, as already set forth. All projections that were measured in these resting phases of the heart thus be can employed for reconstruction of an image that is low in motion artifacts.

The resting phases of the heart are referenced R in FIG. 9 and the motion phases are referenced B.

Figure 10:
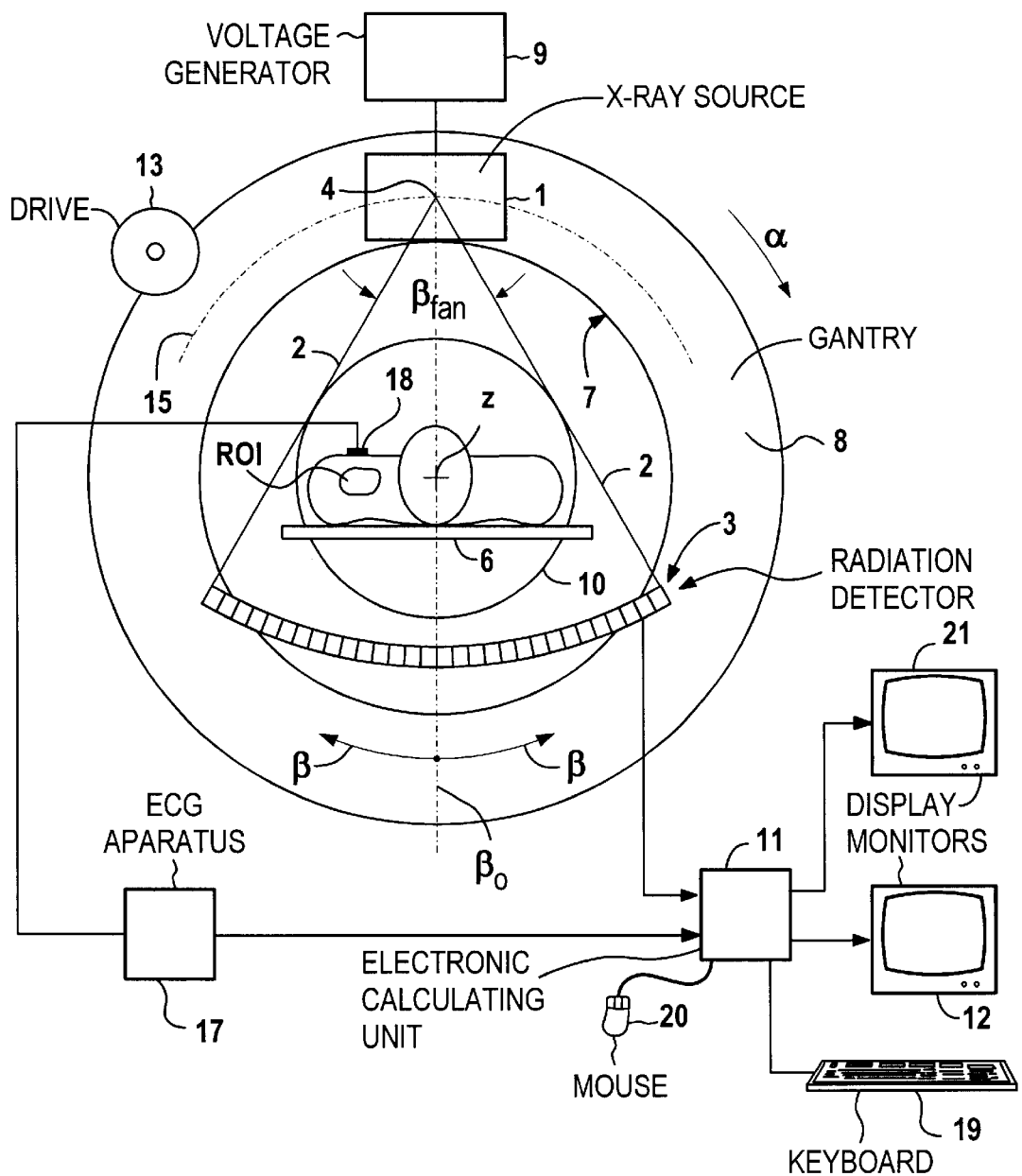
FIG. 10 shows a CT apparatus suitable for the implementation of the inventive method.

FIG. 10 schematically shows a CT apparatus for the implementation of the disclosed method.

The CT apparatus has a measuring unit composed of an x-ray source 1 that emits a fan-shaped x-ray beam 2, and a detector 3 that is composed of one or more lines of individual detectors, for example 512 individual detectors, following one another in the z-direction. The focus of the x-ray source 1, from which the x-ray beam 2 emanates, is referenced 4. An examination subject, a human patient 5 in the exemplary embodiment, lies on a support table 6 that extends through the measuring opening 7 of a gantry 8.

The x-ray source 1 and the detector 3 are attached to the gantry 8 lying opposite one another. The gantry 8 is mounted so as to be rotatable around the z-axis of the CT apparatus, referenced z, that represents the system axis, and is rotated around the z-axis in the direction of the arrow referenced α for scanning the patient 5 in the α-direction, namely by an angle that amounts to at least 180° (π)+fan angle (aperture angle of the fan-shaped x-ray beam 2). The x-ray beam 2 emanating from the x-ray source 1, which is operated with a voltage generator 9, covers a measuring field 10 having a circular cross section. The focus 4 of the x-ray source 1 moves on a focus path 15 which is circularly curved around the rotational center lying on the z-axis.

Measured values referred to as projections are registered at predetermined angular positions of the measuring unit 1, 3, referred to as the projection angles. The corresponding measured data proceed from the detector 3 to an electronic calculating unit 11 that, using measuring points from sequences corresponding to the projections, reconstructs the attenuation coefficients of the picture elements of a picture element matrix and graphically reproduces this on a viewing monitor 12, on which, thus, images of the slices of the patient 5 covered by the projections appear.

Each projection P(n,k) has a projection number n by which the projection is allocated to a specific angular position, i.e. to a projection angle, and covers a number of measuring points corresponding in number to the number of detector elements, i.e. the channel number K, to which the corresponding measured value is respectively allocated. The respective channel number k indicates from which detector elements, having the continuous channel numbers $k_1$ through $k_k$, the respective measured value derives, with the central channel corresponding to the middle detector element of a row of detector elements.

When the detector 3 has multiple lines of detector elements, a number of slices of the patient 5 can be simultaneously registered as needed, with a number of projections corresponding in number to the number of active detector lines, then being registered.

The drive 13 allocated to the gantry 8 can produce not only a sub-revolution or full revolution of the gantry 8, but also can allow the gantry 8 to continuously rotate. When a further drive is also provided that enables a relative displacement between the support table 6, and thus the examination subject 5 and the gantry 8 with the measuring unit 1, 3 in the z-direction, as spiral scans can also be implemented.

For implementation of examinations of the heart or of heart-proximate regions of the body of the patient 5 moving in the rhythm of the heart action, the CT apparatus of FIG. 1 also has a known ECG apparatus 17 that can be connected to the patient 5 via electrodes, one thereof being shown in FIG. 1 and being referenced 18, which serves for the acquisition of the ECG signal of the examination subject 5 in parallel with the examination with the CT apparatus. Preferably digital data corresponding to the ECG signal are supplied to the electronic calculating unit 11.

Insofar as possible, the electrodes of the electrocardiograph 17 are attached to the body of the patient 5 so that they do not negatively influence the examination of the patient 5.

A keyboard 19 and a mouse 20 that enable the operation of the CT apparatus are connected to the electronic calculating unit 11. Moreover, a further monitor 21 is connected to the electronic calculating unit 11, on which operating menus are displayed as explained in greater detail below and illustrated in FIGS. 12 through 14.

Figure 11:
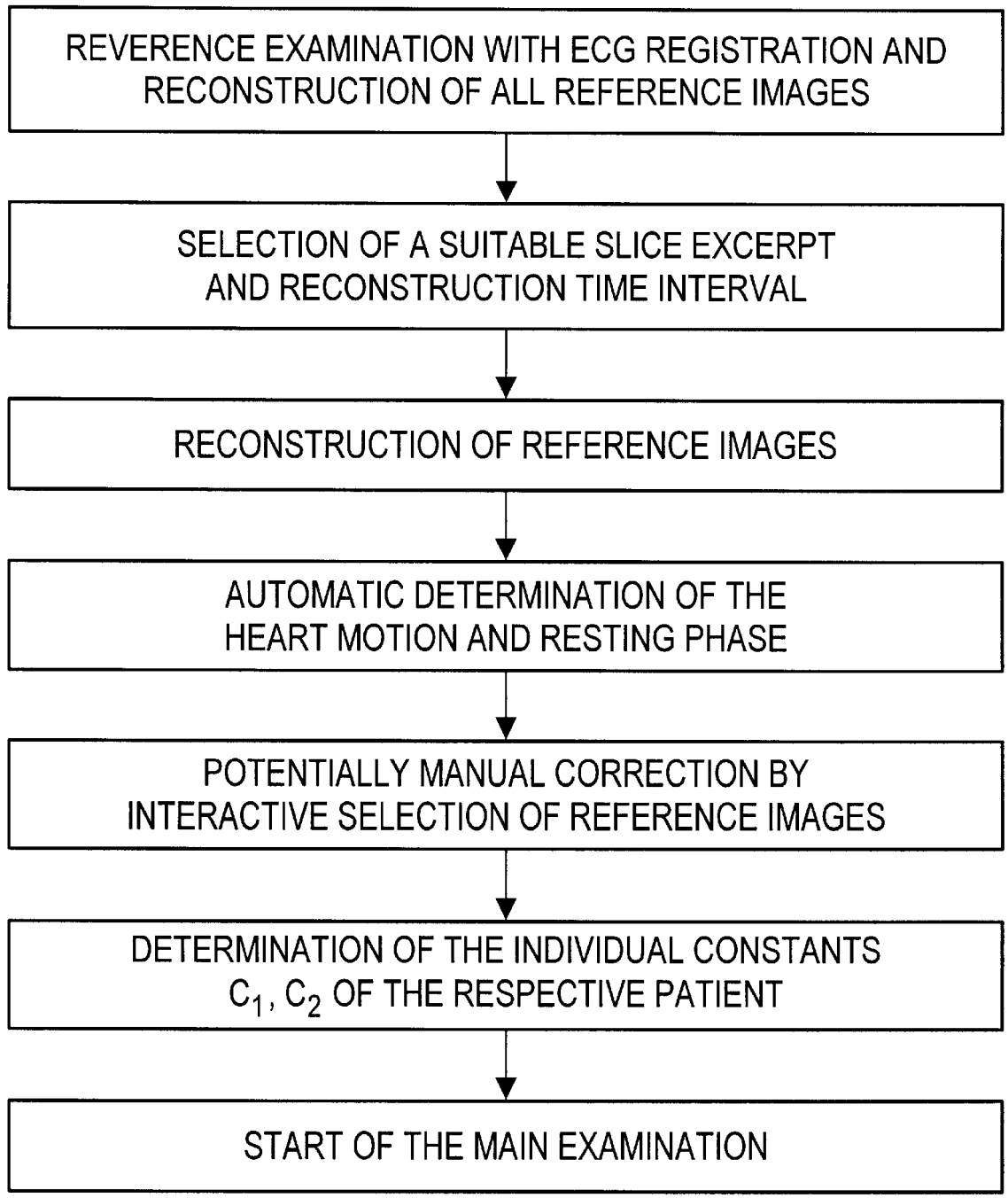
FIG. 11 is a flowchart of the reference examination for determining the resting heart phase.

As an example, FIG. 11 shows an overview of the execution of a reference examination implemented with the CT apparatus according to FIG. 10 before the actual examination, i.e. the main examination, for determining the constants $C_1$ and $C_2$ for the definition of the resting phases of the heart on the basis of the ECG signal using combined automatic and/or interactive evaluation.

Figure 12:
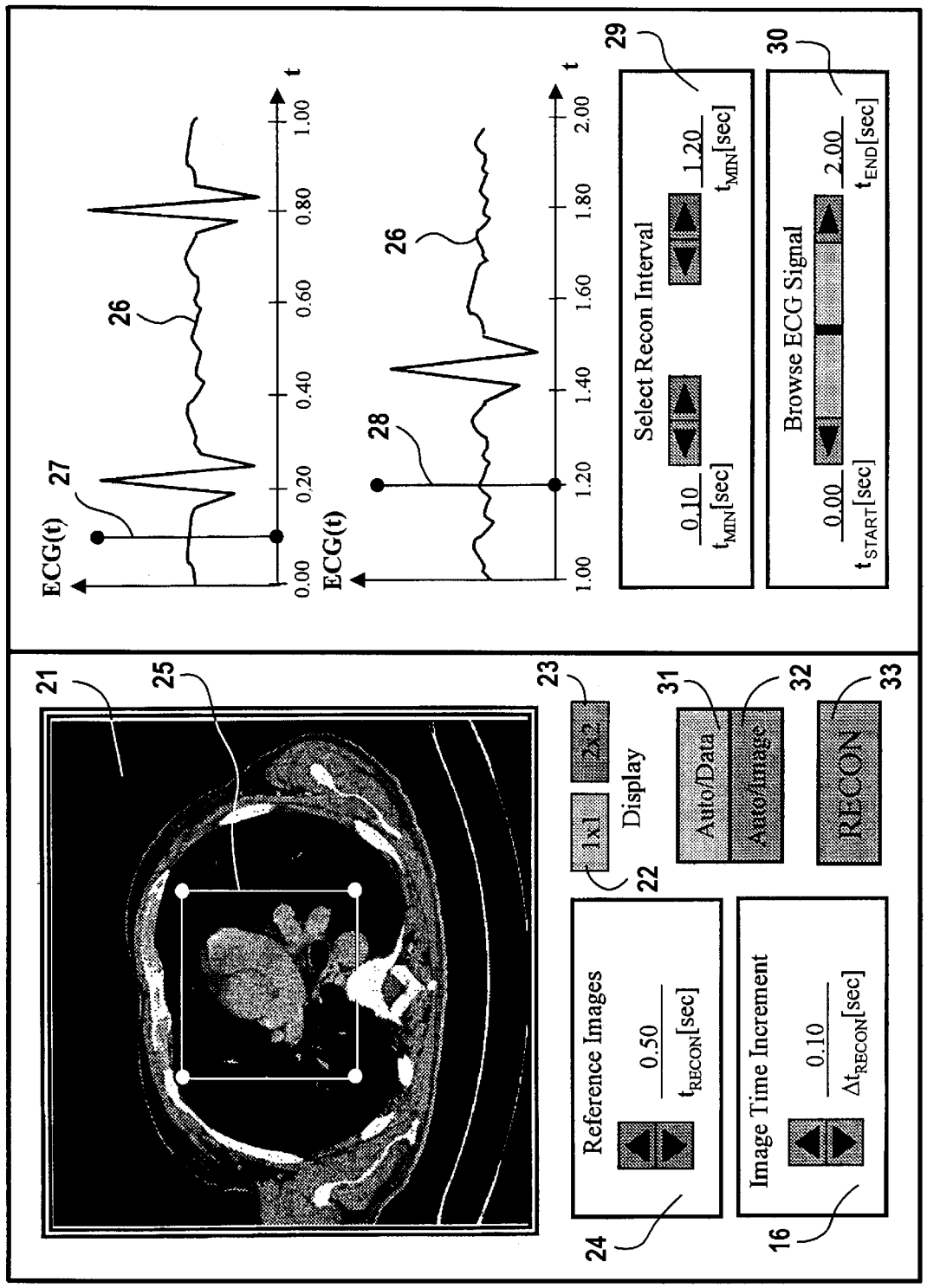
FIG. 12 shows an operating menu for implementation of the reference examination for determining the resting heart phase.
Figure 13:
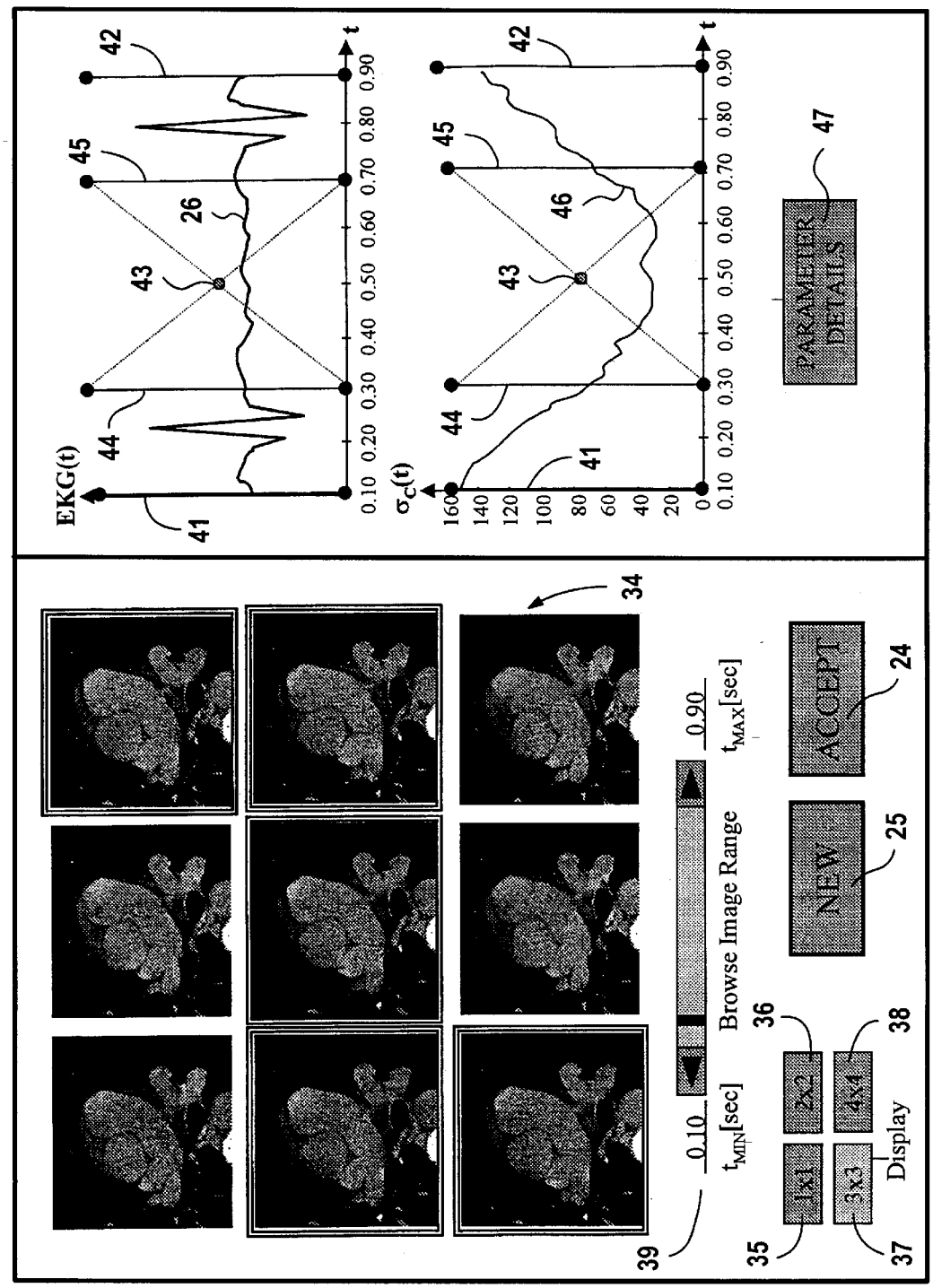
FIG. 13 shows an operating menu for determining the resting heart phase.
Figure 14:
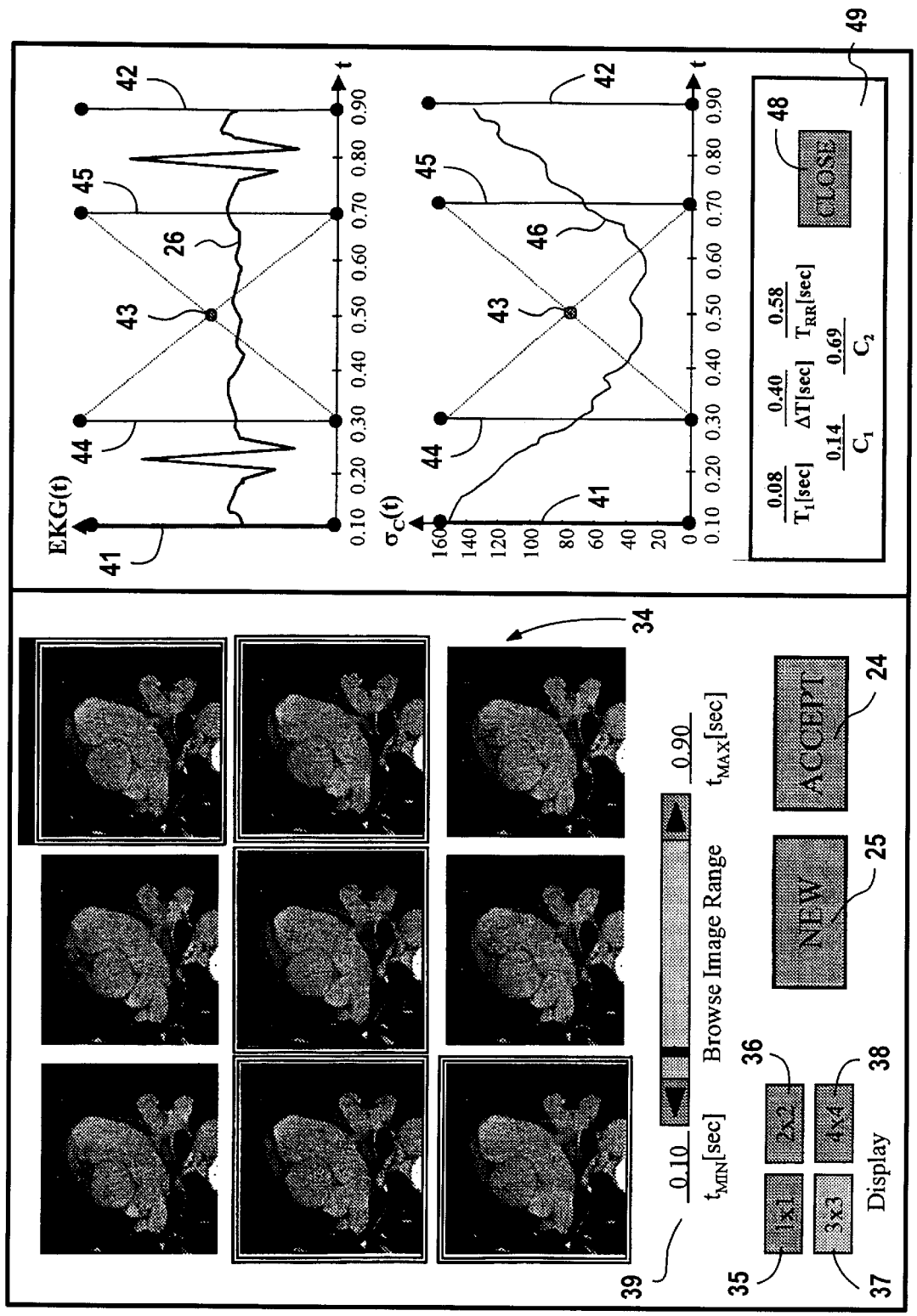
FIG. 14 show an operating menu for determining the resting heart phase with opened parameter window.

FIGS. 12 through 14 show the corresponding operating menus that appear on the screen of the monitor 14 during implementation of the reference examination in the fashion of a known graphic user interface that is operable, for example, with the mouse 20, the functioning thereof being described below.

After registration of the test projections, tomograms of the region of the patient P located in the measuring field 10 are reconstructed in a coarse time grid (for example, 0.5 s). These images are shown in the upper left region 21 of the first operating menu illustrated in FIG. 12. By actuating buttons 22, 23, there is the possibility of selecting various divisions of the region 21, for example the division 1×1 or the division 2×2. In the former instance, as shown in FIG. 12, an image filling the entire region 21 is presented, whereas in the latter instance, four correspondingly smaller images would be presented in two rows and columns. Moreover, a selection field 24 is present with which the coarse time grid in which the reference images are reconstructed can be set.

For automatic determination of the strength of the motion artifacts which are present in the reference images, there is the possibility of selecting the relevant image field with a region of interest (ROI) 25 that, for example, can be circular or, as shown in FIG. 12, rectangular.

The ROI 25 can be modified in position and size with, for example, the mouse 20 or with some other suitable input means that is not shown.

The normally finer time grid wherein the reconstruction of the images on which the image-oriented and/or automatic determination of the resting phase of the heart ensues is set in the selection field 16.

The ECG signal 26 acquired with the ECG apparatus 17 is shown as a function of the time t in the right region of the first operating menu. In the exemplary embodiment, this ensues in two sections arranged above one another and adjoining one another in time that cover a total of two seconds.

The reconstruction time interval wherein the test images are to be reconstructed is determined, for example, interactively by inserting a start mark 27 and an end mark 28 into the ECG signal 26. The start and end marks 27 and 28 can be shifted with the selection field 9 in conformity with the respective requirements, with the position of the start mark 27 corresponding to the time $t_{MINS}$ and the position of the end mark 28 corresponding to the time $t_{MAX}$.

When the range of presentation of the ECG signal 26 that is offered is unsuitable, this can be displaced with the assistance of the selection field 30. The time $t_{START}$ thereby corresponds to the beginning of the illustrated section of the ECG signal 26, and the time $t_{END}$ corresponds to the end of the illustrated section of the ECG signal 26. A line mark on a scale belonging to the selection field indicates the middle of the illustrated section of the ECG signal 26.

It is possible to select the method underlying the automatic determination of the resting phase of the heart with the buttons referenced 31 and 32. When the button 31 labeled auto/data is actuated, the automatic determination ensues on the basis of the described comparison of complementary parallel projections. When, by contrast, the button 32 labeled auto/image is actuated, the automatic determination of the resting phase of the heart ensues on the basis of the described, automatic detection of motion artifacts.

The actuation of the button 33 labeled RECON starts the reconstruction of the test images in the reconstruction time interval predetermined with the selection field 29 and in the time grid predetermined with the selection field 16, and also starts the automatic determination of the resting heart phase according to the method selected with the buttons 31 and 32.

The operating menu according to FIG. 13 appears subsequent thereto.

This indicates the reconstructed test images in a region 34 serving the purpose of image presentation. Only the image excerpt corresponding to the ROI 25 is shown, namely with a subdivision of the region 34 into 1×1 through 4×4 test images selectable with the buttons 35 through 38.

Those test images that were allocated to the resting phase in the automatic determination of the resting phase of the heart are marked with a boundary (outline).

The time interval from which the test images displayed in the region 34 originate can be varied with the selection field 39, with $t_{MIN}$ representing the starting time and $t_{MAX}$ representing the ending time of the time interval covered by the presentation of test images. A line mark on a scale belonging to the selection field 39 indicates the middle of this time interval.

The section of the ECG signal 26 corresponding to the time interval covered by the presentation of test images is shown in the upper right region of the second operating menu. As shown in FIG. 13, there is the possibility of mixing a corresponding start mark 41 and an end mark 42 into the ECG presentation. Moreover, the automatically determined resting phase 43 can be mixed into the presentation of the ECG signal 26 with corresponding start and end marks 44 and 45.

If the automatic determination of the resting phase of the heart ensued by comparing complementary parallel projections, the curve of the complementary error criterion $\sigma_C$ is shown as a function of the time t for the time interval corresponding to the presentation of the ECG signal 26. Analogous to the presentation of the ECG signal 26, moreover, the resting phase 43 is mixed in with the start and end marks 44 and 45.

When the button 47 labeled PARAMETER DETAILS is actuated, the currently determined constants $C_1$ and $C_2$ for definition of the resting phase of the heart within arbitrary RR intervals as well as the calculation basis thereof, i.e. the values for $\Delta_T$, $T_{RR}$ and $T_1$, are displayed in a parameter window 49 in an operating menu shown in FIG. 14 that otherwise conforms to the operating menu according to FIG. 13. The parameter window 49 closes, i.e. the operating menu according to FIG. 13 appears again, by actuation of the button 48 labeled CLOSE.

The functioning of the operating menus shown in FIGS. 12 through 14 thus gives an operator the possibility of interactively influencing the automatically determined position of the resting phase of the heart and correcting this as needed, both by interventions in the region 34 serving the purpose of presenting test images as well as in the presentation of the ECG signal 26 and in the presentation of the complementary error criterion 46. These regions of the operating menu are logically linked for this purpose.

The selection and deselection of test images, for example with the mouse 20, is possible in the region 34. The selected test images marked with the boundary are allocated to the resting heart phase. The definition region of the resting phase of the heart is adapted by corresponding, automatic displacement of the start and end marks 44 and 45 in the presentation of the ECG signal 26 and of the complementary error criterion 46, and the values displayed in the parameter window 49 are corresponding modified or recalculated. When the time interval illustrated in the region 34 by test images is modified, the time axes and the positions of the start and end marks 41 and 42 or of the start and end marks 44 and 45, correspondingly change in the presentation of the ECG signal 26 and of the complementary error criterion 46.

Conversely, the time span illustrated in the region 34 by test images as well as the resting phase 43 can be interactively modified in terms of duration and position in the presentation of the ECG signal 26 and of the complementary error criterion 46, namely by displacing the start and end marks 41 and 42, or the start and end mark 44 and 45. The selection of the images presented in the region 34 and the marking of test images lying the resting phase of the heart is then correspondingly adapted.

When the operator accepts the definition of the resting phase of the heart, the calculated constants $C_1$ and $C_2$ can be accepted for the following, actual examination by actuating the button 24 labeled ACCEPT. A further, conventional operating menu (not shown) then opens for setting the operating parameters for the actual examination.

If no satisfactory result was able to be achieved in the definition of the resting phase of the heart, the operator can return to the operating menu shown in FIG. 12 by actuating the button 25 referenced NEW and can select modified values to be used for a renewed determination of the resting phase of the heart ensues in the above-described way.

When the determination of the resting phase of the heart ensues without acquisition of the ECG of the patient, the operating menu required for the determination of the resting phase of the heart is limited to the presentation of a reference image wherein the ROI required for the automatic determination of the resting phase of the heart can be marked, i.e. the operating menu essentially corresponds to the region 21 shown in FIG. 12. The actual examination can be started directly following the selection of a ROI.

The CT apparatus described in the exemplary embodiment is an apparatus of the third generation. The invention, however, can also be employed in conjunction with an apparatus of the fourth generation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing computed tomography images of a body region in an examination subject, said body region exhibiting a substantially periodic movement cycle containing a resting phase and a motion phase, comprising the steps of:

rotating a focus of an x-ray source around said examination subject through at least one revolution during a time duration that is at least equal to a duration of said cycle, and registering a plurality of sets of projection data, said different sets of projection data respectively representing x-rays attenuated by said examination subject from a plurality of different projection angles;

analyzing said sets of projection data to determine whether each set of projection data was acquired during a resting phase or a motion phase of said cycle; and reconstructing an image of said body region of said examination subject using only data from said sets of projection data that are determined by the analyzing of said sets of projection data to have been obtained during a resting phase of said cycle.

2. A method as claimed in claim 1 wherein said sets of projection data include sets of projection data from complementary parallel projections, and wherein the step of analyzing said data comprises identifying a deviation $\sigma(n)$ of said complementary parallel projections from each other, and designating parallel projections wherein said deviation $\sigma(n)$ does not exceed an upper limit $\sigma_{C,S}$ as representing data acquired during a resting phase, wherein n is a projection number.

3. A method as claimed in claim 2 comprising calculating said deviation $\sigma_c(n)$ according to:

$$\sigma_c(n) = \text{SUM}_{(k=Ka(1)Kc)}\{\text{ABS}[P(N+n, K-k-1) - P(n,k)]\},$$

wherein $P(n,k)$ designates a parallel test projection, n is a number of said parallel test projections measured through a revolution of 180° of said x-ray source focus, K designates a number of channels per parallel test projection, k designates a channel number $K_a$ designates a start channel and $K_c$, designates an end channel.

4. A method as claimed in claim 2 comprising using only complementary parallel projections from a designated region of interest of said examination subject.

5. A method as claimed in claim 4 comprising the step of generating a reference image for identifying said region of interest before registering said plurality of sets of projection data.

6. A method as claimed in claim 2 comprising acquiring a plurality of sets of fan projection data as said plurality of sets of projection data, and producing said parallel projections by resorting and re-interpolating said plurality of sets of fan projection data.

7. A method as claimed in claim 1 wherein the step of analyzing said data comprises:
reconstructing a plurality of test images respectively from at least some of said plurality of sets of projection data;
checking each of said plurality of test images for a presence of motion artifacts therein; and
identifying at least one usable time interval during which a magnitude of said motion artifacts respectively in said test images does not exceed an upper limit, and designating only those sets of projection data that were obtained within said usable time interval as being acquired during a resting phase.

8. A method as claimed in claim 7 comprising selecting artifacts from the group of artifacts consisting of line artifacts and double contours for checking said test images for the presence of motion artifacts.

9. A method as claimed in claim 7 wherein the step of checking said test images for the presence of motion artifacts comprises obtaining difference images by subtraction of successive ones of said test images.

10. A method as claimed in claim 7 comprising reconstructing said plurality of test images using computer performance which is reduced in comparison to a computer performance used for reconstructing said body region of said examination subject.

11. A method as claimed in claim 7 comprising reconstructing said plurality of test images using resolution which is reduced in comparison to a resolution used for reconstructing said body region of said examination subject.

12. A method as claimed in claim 7 comprising reconstructing said plurality of test images using data from said plurality of sets of projection data obtained during less than a complete revolution of said x-ray source focus around said examination subject.

13. A method as claimed in claim 7 comprising checking each of said plurality of test images for the presence of motion artifacts only for a selected region of interest in said test images.

14. A method as claimed in claim 13 comprising identifying said region of interest from one of said test images.

15. A method as claimed in claim 7 comprising the additional step of obtaining an ECG signal from said subject while obtaining said plurality of sets of projection data, said ECG signal containing successive R-waves, and wherein the step of analyzing said data comprises identifying a usable time interval between two of said successive R-waves relative to said data acquired during a resting phase, and subsequently using only data acquired during said usable time interval for reconstructing said image of said body region of said examination subject.

16. A method as claimed in claim 1 comprising the additional step of obtaining an ECG signal from said subject while obtaining said plurality of sets of projection data, said ECG signal containing successive R-waves, and wherein the step of analyzing said data comprises identifying a usable time interval between two of said successive R-waves relative to said data acquired during a resting phase, and subsequently using only data acquired during said usable time interval for reconstructing said image of said body region of said examination subject.

17. A method as claimed in claim 16 comprising defining said usable time interval as beginning at a predetermined, first fraction of a heart cycle of said examination subject following an R-wave initiating said heart cycle and having a duration equal to a second, predetermined fraction of said heart cycle.

18. A method as claimed in claim 1 wherein the step of analyzing said data comprises:
before obtaining said plurality of sets of projection data, registering data for a plurality of test projections during at least one revolution of said focus of said x-ray source around said examination subject and during a time duration that is at least equal to said cycle of movement of said body region, said plurality of test projections including a plurality of complementary parallel test projections, while simultaneously acquiring an ECG signal from said examination subject, said ECG signal comprising a plurality of successive R-waves;
identifying deviations $\sigma_c(n)$ of said complementary parallel test projections from each other, wherein n is a complementary test parallel projection number;
identifying a usable time interval between two of said successive R-waves of said ECG signal during which said deviations $\sigma_c(n)$ do not exceed an upper limit $\sigma_{c,s}$;
acquiring a subsequent ECG signal from said patient while obtaining said plurality of sets of projection data and identifying a time relative to said ECG signal at which each of said plurality of sets of projection data was obtained; and
employing only those sets of projection data for reconstructing said image of said body region of said examination subject which were acquired during said usable time interval.

19. A method as claimed in claim 18 comprising calculating said deviation $\sigma_c(n)$ according to:

$$\sigma_c(n) = \text{SUM}_{(k=Ka(1)Ke)}\{\text{ABS}[P(N+n,K-k-1)-P(n,k)]\},$$

wherein P(n,k) designates a parallel test projection, n is a number of said parallel test projections measured through a revolution of 180° of said x-ray source focus, K designates a number of channels per parallel test projection, k designates a channel number $K_a$ designates a start channel and $K_e$ designates an end channel.

20. A method as claimed in claim 18 comprising using only complementary parallel test projections from a designated region of interest of said examination subject.

21. A method as claimed in claim 20 comprising the step of generating a reference image for identifying said region of interest before registering said plurality of sets of projection data.

22. A method as claimed in claim 18 comprising acquiring a plurality of sets of fan projection data as said plurality of sets of projection data, and producing said parallel projections by resorting and re-interpolating said plurality of sets of fan projection data.

23. A method as claimed in claim 18 comprising defining said usable time interval as beginning at a predetermined, first fraction of a heart cycle of said examination subject following an R-wave initiating said heart cycle and having a duration equal to a second, predetermined fraction of said heart cycle.

24. A method as claimed in claim 1 wherein the step of analyzing said data comprises:
before obtaining said plurality of sets of projection data, registering data for a plurality of test projections during at least one revolution of said focus of said x-ray source around said examination subject and during a time duration that is at least equal to said cycle of movement of said body region, said plurality of test projections including a plurality of complementary parallel test projections, while simultaneously acquiring an ECG signal from said examination subject, said ECG signal comprising a plurality of successive R-waves;

reconstructing a plurality of test images respectively from said test projections;

checking each of said test images to identify a presence of motion artifacts respectively in the test images;

identifying a usable time interval between two of said successive R-waves of said ECC signal during which a magnitude of said motion artifacts in a plurality of successive ones of said test images does not exceed an upper limit; and reconstructing said image of said body region of said examination subject using only data acquired during said usable time interval as said data acquired during a resting phase.

25. A method as claimed in claim 24 comprising selecting artifacts from the group of artifacts consisting of line artifacts and double contours for checking said test images for the presence of motion artifacts.

26. A method as claimed in claim 24 wherein the step of checking said test images for the presence of motion artifacts comprises obtaining difference images by subtraction of successive ones of said test images.

27. A method as claimed in claim 24 comprising reconstructing said plurality of test images using computer performance which is reduced in comparison to a computer performance used for reconstructing said body region of said examination subject.

28. A method as claimed in claim 24 comprising reconstructing said plurality of test images using resolution which is reduced in comparison to a resolution used for reconstructing said body region of said examination subject.

29. A method as claimed in claim 24 comprising reconstructing said plurality of test images using data from said plurality of sets of projection data obtained during less than a complete revolution of said x-ray source focus around said examination subject.

30. A method as claimed in claim 24 comprising checking each of said plurality of test images for the presence of motion artifacts only for a selected region of interest in said test images.

31. A method as claim 30 comprising identifying said region of interest from one of said test images.

32. A computed tomography apparatus comprising:

an x-ray source having a focus which rotates around an examination subject containing a body region exhibiting a motion cycle having a resting phase and a motion phase;

a control unit for operating said x-ray source to obtain a plurality of sets of projection data during at least one revolution of said x-ray source around said examination subject during a time duration that is at least equal to a duration of said movement cycle, said sets of projection data respectively representing attenuation of x-rays from said x-ray source by said examination subject at a plurality of different projection angles;

a computer supplied with said plurality of sets of projection data for reconstructing a plurality of test images from the respective sets of projection data;

a display connected to said computer on which said computer displays said test images;

an input unit interacting with said computer and said display allowing identification of selected ones of said test images which are low in motion artifacts;

said computer subsequently identifying a usable time interval based on said test images identified as being low in motion artifacts, during which data can subsequently be obtained as data within a resting phase of said motion cycle;

said control unit subsequently operating said x-ray source to obtain a plurality of subsequent sets of projection data; and said computer using only data from said subsequent sets of projection data which are obtained during said usable time interval.

\* \* \* \* \*